United States Patent [19]

Umezawa et al.

[11] Patent Number: 4,495,347
[45] Date of Patent: Jan. 22, 1985

[54] ANTIBIOTIC OXANOSINE AND PROCESS FOR THE PREPARATION THEREOF

[75] Inventors: Hamao Umezawa; Nobuyoshi Shimada, both of Tokyo; Hiroshi Naganawa, Honmachi; Tomohisa Takita, Asaka; Masa Hamada, Naito; Tomio Takeuchi, Tokyo, all of Japan

[73] Assignee: Zaidan Hojin Biseibutsu Kagaku Kenkyu Kai, Tokyo, Japan

[21] Appl. No.: 439,446

[22] Filed: Nov. 5, 1982

Related U.S. Application Data

[62] Division of Ser. No. 323,650, Nov. 20, 1981, Pat. No. 4,394,446.

[30] Foreign Application Priority Data

Nov. 22, 1980 [JP] Japan .................................. 55-165159

[51] Int. Cl.$^3$ ........................................... C07H 17/00
[52] U.S. Cl. ...................................... 536/24; 514/908
[58] Field of Search .......................................... 536/24

[56] References Cited

PUBLICATIONS

Chemical Abstracts 99:071119 (1983).
Chemical Abstracts 97:143134 (1982).
Chemical Abstracts 97:066047 (1982).
Chemical Abstracts 96:085911 (1982).
Chemical Abstracts 96:048667 (1982).
Chemical Abstracts 96:031279 (1982).
Journal of Antibiotics, 34, (9) 1216–1221, (Sep. 1981).

Primary Examiner—Ethel G. Love
Attorney, Agent, or Firm—Richard R. Lloyd

[57] ABSTRACT

The novel antibiotic, oxanosine, having the structure

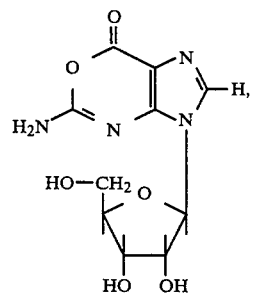

inhibits the growth of Gram-negative bacteria and has antiviral activity. It is produced by cultivation of an oxanosine-producing microorganism of the genus Streptomyces, preferably *Streptomyces capreolus* MG265-CF3, ATCC No. 31963.

1 Claim, 3 Drawing Figures

ULTRAVIOLET ABSORPTION SPECTRA OF OXANOSINE
——— $H_2O$
- - - - 0.1N HCl
— — — 0.1N NaOH $^1H$ NMR SPECTRUM OF OXANOSINE
(100 MHz IN DEUTERATED DMSO)

ANTIBIOTIC OXANOSINE AND PROCESS FOR THE PREPARATION THEREOF

CROSS REFERENCE TO RELATED APPLICATION

This application is a divisional of our prior, copending application Ser. No. 323,650, filed Nov. 20, 1981, now U.S. Pat. No. 4,394,446.

SUMMARY OF THE INVENTION

Oxanosine, a novel antibiotic of the formula

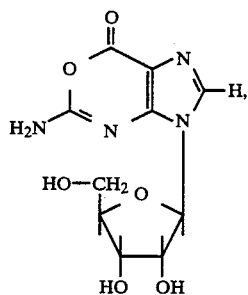

exhibits relatively strong inhibitory activity against various Gram-negative bacteria, and has antiviral activity. It is produced by culturing an oxanosine-producing strain of Streptomyces such as *Streptomyces capreolus* MG265-CF3 (ATCC No. 31963) or a mutant thereof.

DETAILED DESCRIPTION OF THE INVENTION

Figure 1:
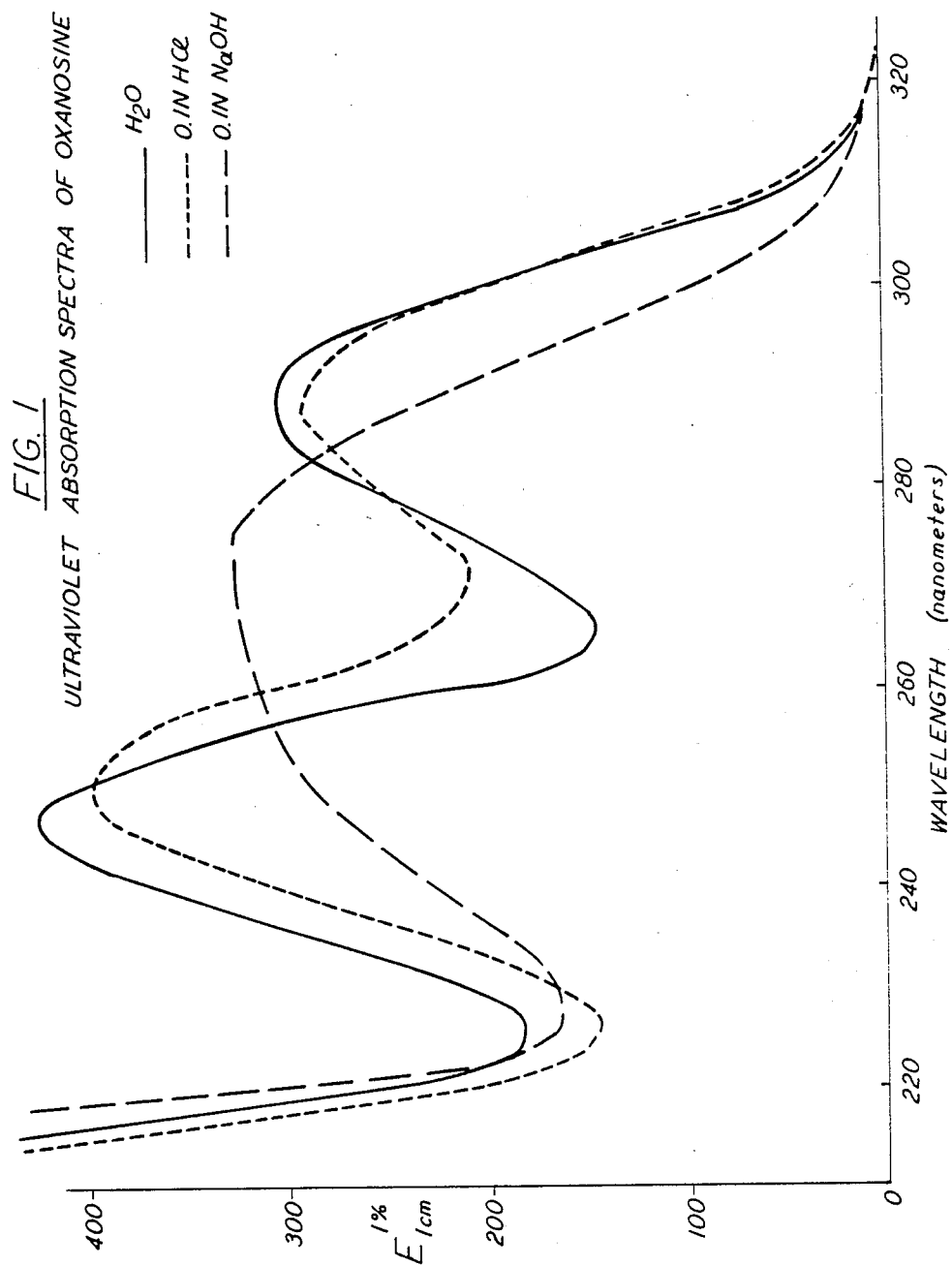
FIG. 1 shows the ultraviolet absorption spectra of oxanosine in water, 0.1N HCl and 0.1N NaOH.

The present invention relates to oxanosine, a novel antibiotic having the formula

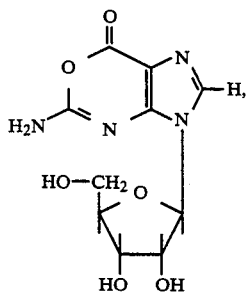

to a process for the preparation thereof, and to the novel microorganism which produces it.

Oxanosine, the novel antibiotic of the present invention, exerts a growth-inhibiting action against Gram-negative bacteria and has antiviral actions and, therefore, oxanosine is valuable as a medicine.

The novel antibiotic oxanosine is obtained by culturing an oxanosine-producing microorganism belonging to the genus Streptomyces, accumulating oxanosine produced by said microorganism, and collecting the antibiotic oxanosine from the culture broth. A preferred oxanosine-producing microorganism is the strain of *Streptomyces capreolus* MG265-CF3 isolated from soil collected at the compound of the Institute of Microbial Chemistry in July 1979, and mutants thereof. This strain MG265-CF3 was deposited in the Fermentation Research Institute, Agency of Industrial Science and Technology (located at Yatabe-cho, Tsukuba-gun, Ibaragi-ken, Japan) under deposit number FERM-P 5735 on Oct. 6, 1980 and in the American Type Culture Collection, Parklawn Drive, Rockville, Md., U.S.A., under deposit number ATCC 31963 on Sept. 14, 1981.

MYCOLOGICAL PROPERTIES OF STRAIN MG265-CF3

(A) Morphology

Under a microscope, it is seen that the strain MG265-CF3 forms relatively long, straight aerial mycelia from branched substrate mycelia, but the formation of spirals or loops is not observed. Mature spore chains include at least 10 spores, and the size of the spores is (0.4–0.5 micron)×(1.5–2.4 microns). The surfaces of the spores are smooth.

(B) Cultural Characteristics of Various Culture Media

Parenthesized colors are described according to "Color Harmony Manual" of the Container Corporation of America.

(1) Sucrose-nitrate Agar (cultured at 27° C.):

White to brownish-white [3ba, Pearl] aerial mycelia adhere to a colorless, pale yellow or pale yellowish-brown [21e, Mustard] growth, and a soluble pigment giving a faint yellowish tint is produced.

(2) Glucose-asparagine Agar (cultured at 27° C.):

White aerial mycelia adhere thinly to a pale yellow to pale yellowish-brown [2gc, Bamboo to 3ic, Lt. Amber] growth, and a soluble pigment giving a faint yellowish tint is formed.

(3) Glycerol-asparagine Agar Medium (ISP Medium 5 cultured at 27° C.):

White to yellowish-gray aerial mycelia adhere thinly to a colorless, pale yellow or pale yellowish-brown [2gc, Bamboo to 3ne, Topaz] growth, and a soluble pigment giving a faint yellowish tint is formed.

(4) Inorganic Salt-Starch Agar (ISP Medium 4 cultured at 27° C.):

White aerial mycelia adhere to a colorless to light yellowish-brown [2gc, Bamboo to 2pe, Mustard Gold] growth, and the medium is tinted brown only very slightly. No substantial formation of a soluble pigment is observed.

(5) Tyrosine Agar (ISP Medium 7 cultured at 27° C.):

White to yellowish-gray [3ba, Cinnamon] aerial mycelia adhere to a colorless, pale yellow or pale yellowish-brown [21e, Mustard to 31e, Pearl] growth, and a soluble pigment giving a faint yellowish-brown tint is formed.

(6) Nutrient Agar (cultured at 27° C.):

Growth is colorless to pale yellowish-brown [3ne, Topaz], and adhesion of aerial mycelia is not observed. Formation of a soluble pigment is not observed.

(7) Yeast Extract-Malt Extract Agar (ISP Medium 2 cultured at 27° C.):

White aerial mycelia adhere slightly to a colorless to light yellowish-brown [3ne, Topaz] growth, and formation of a soluble pigment is not observed.

(8) Oat Meal Agar Medium (ISP Medium 3 cultured at 27° C.):

White aerial mycelia adhere to a pale yellow to pale yellowish-brown [2ic, Honey Gold to 2pe, Mustard Gold] growth, and a soluble pigment giving a yellow tint is formed.

(9) Glycarol Nitrate Agar Medium (cultured at 27° C.):

White to pale yellowish-gray [2ba, Pearl] aerial mycelia adhere to a colorless to pale yellowish-brown [2gc, Bamboo to 2ne, Mustard Gold] growth, and a soluble pigment giving a faint yellowish tint is formed.

(10) Starch Agar (cultured at 27° C.):

White to yellowish-gray [3ba, Pearl] aerial mycelia adhere thinly to a colorless, pale yellow or dull yellow-orange [3ic, Lt. Amber to 3ne, Topaz] growth, and formation of a soluble pigment is not observed.

(11) Calcium Malate Agar (cultured at 27° C.):

White to yellowish-gray [3ba, Pearl] aerial mycelia adhere to a colorless to pale yellow [2gc, Bamboo] growth. Formation of a soluble pigment is not observed.

(12) Cellulose (cultured at 27° C.):

White aerial mycelia adhere thickly to a colorless growth, and a soluble pigment giving a faint yellowish-brown tint is formed.

(13) Gelatin Stab Culture (15% plain gelatin, cultured at 20° C.; glucose-peptone gelatin, cultured at 27° C.):

In each culture medium, the growth is colorless to pale yellow, no aerial mycelium adheres and formation of a soluble pigment is not observed.

(14) Skim Milk (cultured at 37° C.):

The growth is pale yellow, pale yellowish-brown or pale yellow-orange [3ic, Lt. Amber] and no aerial mycelium adheres. A pale yellow-orange soluble pigment is formed.

(C) Physiological Properties (1) Growth temperature range:

Culture tests were carried out at 20°, 24°, 27°, 30°, 37° and 50° C. in a glucose-asparagine agar medium. Growth was observed at all temperatures except 50° C., but optimum growth was in the range of from about 30° to about 37° C.

(2) Liquifaction of gelatin (15% plain genatin, cultured at 20° C.; glucose-peptone gelatin cultured at 27° C.):

In case of a plain gelatin medium, liquifaction starts after 10 days from initiation of culturing but liquifaction is not completed within 3 weeks. The liquifaction is moderate to weak. In case of a glucose-peptone gelatin medium, liquifaction of gelatin starts after about 21 days from initiation of culturing. The liquifaction is weak.

(3) Hydrolysis of starch (inorganic salts-starch agar medium and starch agar medium, cultured at 27° C.):

Hydrolysis is observed after 5 days from initiation of culturing, and the hydrolysis activity is moderate to strong.

(4) Coagulation and peptonization of skim milk (cultured at 37° C. in skim milk):

No change is observed during a period of 8 days from initiation of culturing. Coagulation is completed on the 10th day; peptonization starts on the 10th day and is completed on the 21st day. The activity is moderate.

(5) Formation of melanin pigment (tryptone yeast extract broth, ISP Medium 1; peptone-yeast extract-iron agar, ISP Medium 6; tyrosine agar, ISP Medium 7; all cultured at 27° C.):

Formation of a melanin pigment is not observed in any of these culture media.

(6) Utilization of carbon sources (Pridham and Gottlieb agar medium, ISP Medium 9, cultured at 27° C.):

L-Arabinose, D-xylose, D-glucose and D-fructose are utilized for growing, but L-rhamnose, raffinose and D-mannitol are not utilized. It is judged that inositol is probably utilized, and sucrose is utilized in some cases but not utilized in other cases.

(7) Dissolution of calcium malate (calcium malate agar medium, cultured at 27° C.):

Calcium malate is dissolved in the periphery of the growth after 7 days from initiation of culturing, and the dissolving action is moderate to strong.

(8) Reduction of nitrate (aqueous peptone containing 1.0% potassium nitrate, ISP Medium 8, cultured at 27° C.): Negative.

(9) Decomposition of cellulose (cultured at 27° C.): Negative.

When these properties are summarized, the following can be seen. The strain MG265-CF3 belongs to the genus Streptomyces. Neither whirl formation nor spirals are observed on aerial mycelia, and the surfaces of spores are smooth. White to yellowish-gray aerial mycelia adhere to pale yellow, pale yellowish-brown or dull yellow-orange growths on various culture media, and soluble pigments giving only a faint yellow to yellowish-brown tint are formed.

In each culture medium, formation of a melanin is negative, the proteolytic action is moderate to weak and the starch hydrolyzing action is moderate to strong.

When known strains having similar properties were searched for, it was found that *Streptomyces capreolus* [Journal of Systematic Bacteriology, 18, Pages 304–305, 1968 (Reference 1) and Antimicrobial Agents and Chemotherapy, Pages 596–606, 1962 (Reference 2)] is closely related to the strain MG265-CF3.

*Streptomyces capreolus* strain ISP 5225 was actually procured and compared with the strain MG265-CF3. The results of the comparison are summarized in Table 1.

TABLE 1

| | MG265-CF3 | Streptomyces capreolus ISP 5225 |
|---|---|---|
| Aerial mycelium | rectiflexibiles | rectiflexibiles |
| Spore surface | smooth | smooth |
| Color of aerial mycelium | white to yellowish-gray | white to yellowish-gray |
| Color of growth | pale yellow, pale yellowish-brown or dull yellowish-orange | pale yellow, pale yellowish-brown or dull orange |
| Soluble pigment | yellow to yellowish-brown | yellowish-brown to brown |
| Formation of melanin | | |
| ISP Medium 1 | − | − |
| ISP Medium 6 | − | − |
| ISP Medium 7 | − | − |
| Hydrolysis of starch | + | + |
| Coagulation of milk | + | + |
| Peptonization of milk | + | + |
| Liquifaction of gelatin | | |
| plain gelatin | + (moderate to weak) | + (moderate to weak) |
| glucose-peptone gelatin | ± | − |
| Reduction of nitrate | − | − |
| Utilization of | | |

TABLE 1-continued

| | MG265-CF3 | Streptomyces capreolus ISP 5225 |
|---|---|---|
| carbon sources | | |
| D-glucose | + | + |
| L-arabinose | + | + |
| D-xylose | + | + |
| D-fructose | + | + |
| sucrose | + or − | − |
| inositol | ± | − |
| L-rhamnose | − | − |
| raffinose | − | − |
| D-mannitol | − | + (+ or − according to Reference 1) |

NOTE:
"±" -probably positive

As is apparent from the results shown in Table 1, the MG265-CF3 strain is quite in agreement with *Streptomyces capreolus* st. ISP 5225 in coagulation and peptonization of milk, liquifaction of glucose-peptone gelatin and utilization of sucrose, inositol and D-mannitol, except for minor differences. All the cell components of both strains were determined according to thin-layer chromatography and paper chromatography. It was found that both strains contain meso-type diaminopimelic acid (meso-DAP) as the amino acid component, and galactose, glucose and ribose as the sugar components. However, the presence of L-type diaminopimelic acid (LL-DAP), which is an indispensable amino acid component of actinomycetes belonging to the genus Streptomyces, is not observed in *Streptomyces capreolus* ISP 5225 or strain MG265-CF3. Accordingly, it is deemed that further research will be necessary to finally determine whether or not the two strains belong to the genus Streptomyces. The results of the amino acid component analysis are in agreement with those shown in Page 191 of "Classification and Identification of Microorganisms" compiled by Takeji Hasegawa and published by Gakkai Shuppan Center. At any rate, from the foregoing results, it is apparent that strain MG265-CF3 is closely related to *Streptomyces capreolus* strain ISP 5225. Accordingly, the strain MG265-CF3 is presently identified as *Streptomyces capreolus* MG265-CF3.

Oxanosine is prepared by aerobically culturing strain MG265-CF3 in a culture medium containing nutrients utilizable by actinomycetes. Known nutrient sources which have heretofore been used for culturing actinomycetes can be used in the present invention. As the carbon source, there can be used, for example, glucose, glycerol, sucrose, dextrin and galactose, and mixtures thereof. As an inorganic or organic nitrogen source, there can be used, for example, ammonium chloride, ammonium sulfate, urea, ammonium nitrate, sodium nitrate, peptone, meat extract, yeast extract, dry yeast, corn steep liquor, soybean meal, cotton seed meal, Casamino acids, Bacto-soytone, soluble vegetable protein and oat meal. These nitrogen sources may be used singly or in the form of a mixture of two or more of them. Inorganic salts such as sodium chloride, calcium carbonate, magnesium sulfate, copper sulfate, zinc sulfate, iron sulfate, manganese chloride and phosphates may be added according to need. Furthermore, organic substances such as amino acids and nucleic acids, and inorganic substances capable of promoting growth of the strain of the present invention and production of oxanosine, may be added appropriately.

An aqueous culturing method, especially the submerged, stirred, aerobic culturing method, is preferred as the culturing method. It is preferred that culturing be carried out at a temperature of from about 25° C. to about 37° C. under a neutral or weakly acidic pH condition. In the case of aqueous culturing, oxanosine is ordinarily produced and accumulated in the culture broth when culturing is conducted for 3 to 6 days. When the amount of oxanosine reaches maximum, culturing is stopped, the culture broth is filtered and oxanosine is isolated from the filtrate.

Any method customarily adopted for isolation of metabolites of microorganisms from culture broths may be adopted for purification and isolation of the oxanosine of the present invention from the culture filtrate. Oxanosine is soluble in water, methanol and dimethylsulfoxide but insoluble or only slightly soluble in ordinary organic solvents such as ethanol, acetone, ether or benzene. Accordingly, the method customarily used for purification of nucleic acid type antibiotic substances is preferably adopted. For example, an adsorption-desorption method using active carbon powder or a porous adsorbent resin such as Amberlite ®XAD-2 and a column chromatographic method using Avicel ® or Sephadex ®LH-20 may be appropriately combined and used for purification and isolation.

More specifically, the pH value of the culture filtrate is adjusted to 6.5 and the oxanosine is adsorbed on active carbon powder. The active carbon powder is washed with water and elution is then effected with 50% aqueous acetone. The active fraction is concentrated and freeze-dried. The resulting brown crude powder is dissolved in methanol and insoluble substances are removed. The soluble substance is dried and dissolved in water, and the solution is subjected to adsorption treatment with an active carbon powder column. Elution is carried out according to the linear concentration gradient elution method using water and 50% aqueous acetone. The active fraction is concentrated and freeze-dried. The resulting light brown crude powder containing oxanosine is dissolved in a small amount of water and charged on a column of Avicel ®, and development is carried out with aqueous alcohol, and elution is conducted while increasing the water content stepwise. The active fraction is concentrated and freeze-dried. The refined powder is treated with water or aqueous alcohol to obtain needle crystals of oxanosine tinted lightly gray.

The physicochemical properties of oxanosine thus obtained is as follows:

1. Appearance: Grayish-white needle crystals.
2. Molecular Formula (Molecular Weight): $C_{10}H_{12}N_4O_6$ (284.23).
3. Elementary Analysis: Calc'd. C=42.26%, H=4.26%, N=19.71%, O=33.77%. Found C=42.55%, H=4.41%, N=19.84%, O=33.54%.
4. Melting Point: Oxanosine has no definite melting point or decomposition point, but is gradually decomposed at temperatures above 199° C.
5. Specific Rotation: $[\alpha]_D^{23}=36.7$ (C=0.3, $H_2O$).
6. Ultraviolet Absorption Spectra: The ultraviolet absorption spectra are shown in FIG. 1. Ultraviolet absorption and molecular extinction coefficient values in water, 0.1N hydrochloric acid and 0.1N sodium hydroxide are as follows:

$\lambda_{max}^{H_2O}$ (log ε): 247 (4.08), 288 (3.93).
$\lambda_{max}^{0.1N-HCl}$ (log ε): 249 (4.05), 288 (3.91).
$\lambda_{max}^{0.1N-NaOH}$ (log ε): 272 (3.96).

Figure 2:
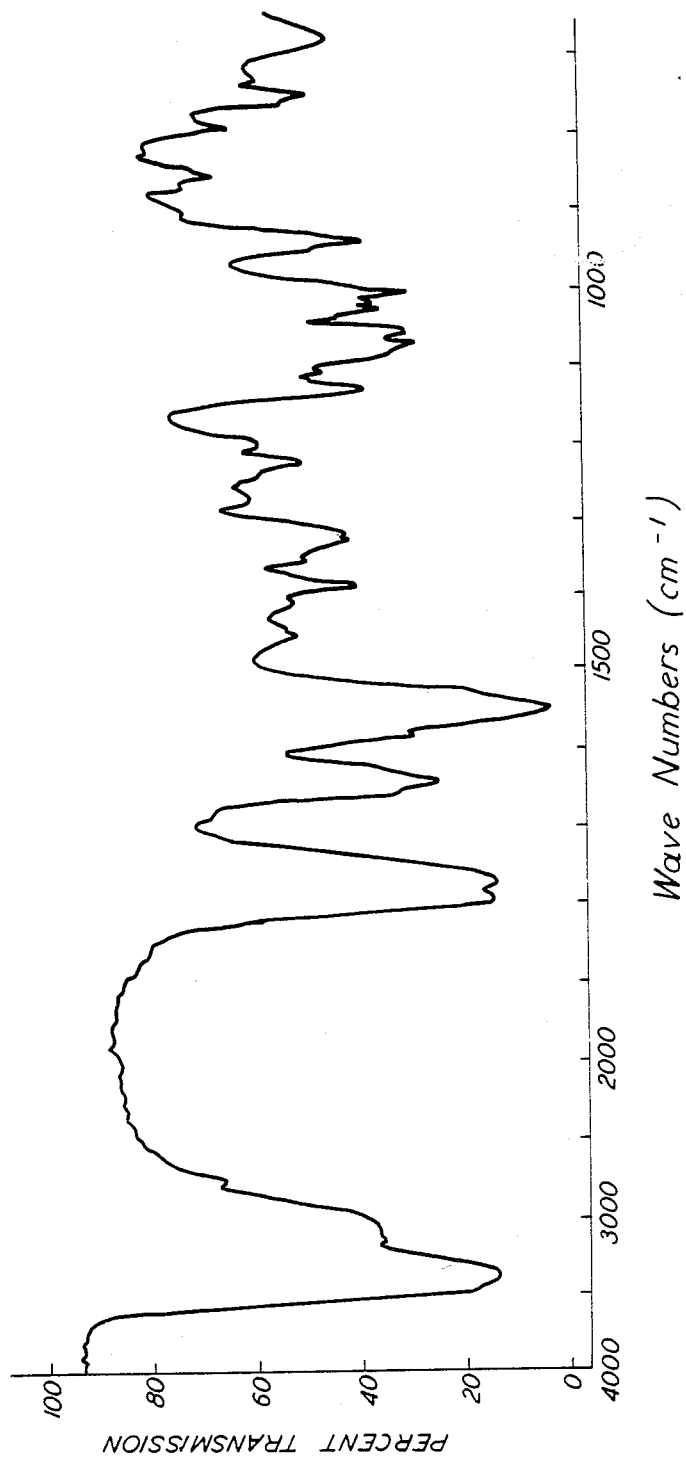
FIG. 2 is the infrared absorption spectrum of oxanosine pelleted in potassium bromide.

7. Infrared Absorption Spectrum: The infrared absorption spectrum determined by using potassium bromide tablets is shown in FIG. 2. The absorption peak values (wave number, cm$^{-1}$) are as follows: 3380, 3100–3000, 2770, 1795, 1770, 1655, 1640, 1585, 1550, 1455, 1410, 1390, 1350, 1325, 1310, 1270–1260, 1240, 1225, 1205, 1195, 1125, 1110, 1085, 1070, 1055, 1030, 1025, 1015, 1005, 990, 950, 940, 905, 870, 855, 845, 820, 795, 760, 750, 730, 675

8. Solubility in Solvents: Soluble in water, methanol and dimethylsulfoxide but insoluble or only slightly soluble in organic solvents such as ethanol, acetone, ethyl acetate, ether and benzene.

9. Color Reactions: Positive to Rydon-Smith reaction and 5% sulfuric acid reaction but negative to ninhydrin reaction, tetrazolium chloride reaction and Sakaguchi reaction.

10. Rf Values in Thin-Layer Chromatography: A silica gel thin layer (Kieselgel 60 F$_{254}$, 0.25 mm. Merck) is used, and development is carried out with n-butanol/acetic acid/water (12/3/5 volume ratio) and n-propanol/pyridine/acetic acid/water (15/10/3/12 volume ratio) and the obtained Rf values are 0.25 and 0.86, respectively.

Figure 3:
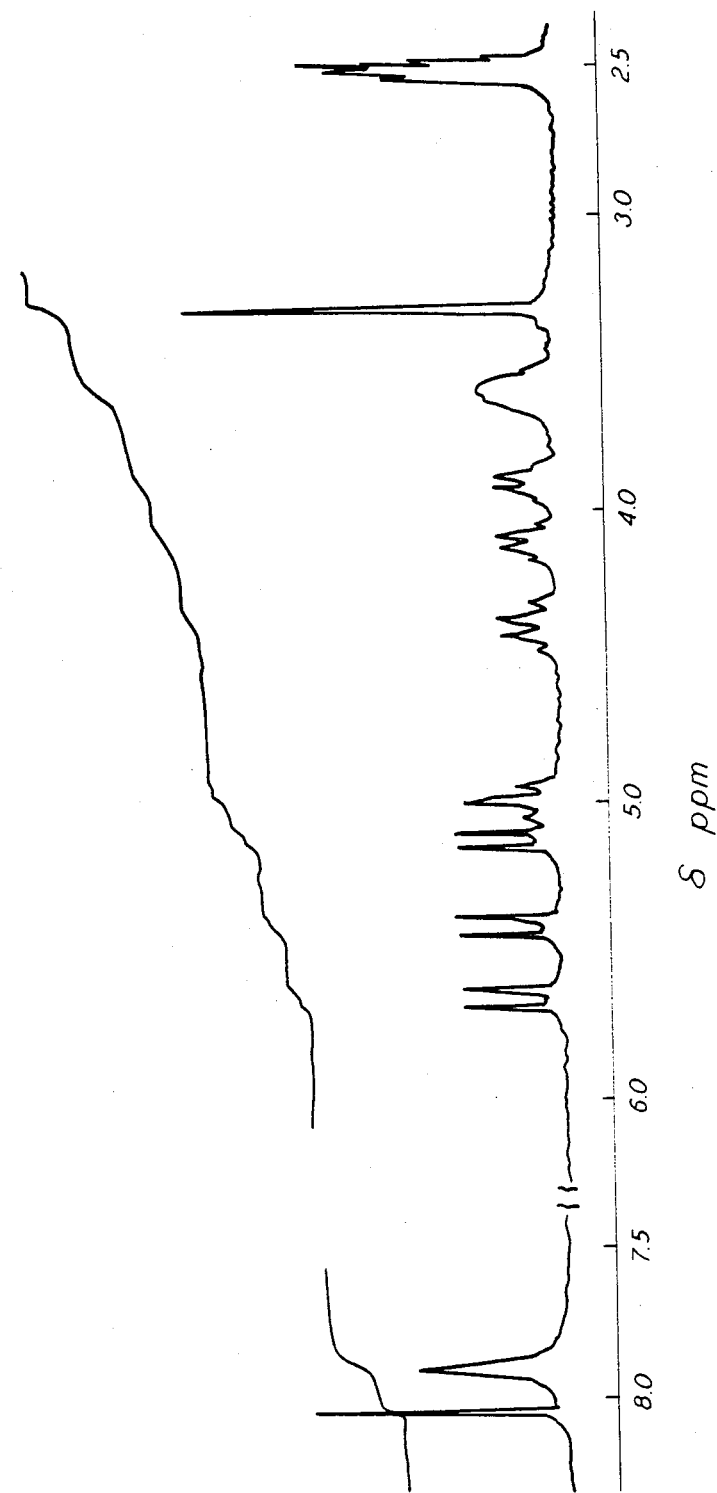
FIG. 3 is the $^1$H-nuclear magnetic resonance spectrum (100 MHz) of oxanosine in deuterated dimethylsulfoxide, using tetramethylsilane as an internal standard.

11. $^1$H-Nuclear Magnetic Resonance Spectrum: The $^1$N-nuclear magnetic resonance spectrum determined in deuterated dimethylsulfoxide by using tetramethylsilane as the internal standard is shown in FIG. 3.

12. $^{13}$C-Nuclear Magnetic Resonance Spectrum: In the $^{13}$C-nuclear magnetic resonance spectrum determined in deuterated dimethylsulfoxide using tetramethylsilane as the internal standard, the chemical shift values (δ values) are as follows: 61.1, 70.3, 73.8, 85.3, 86.5, 110.9, 136.6, 153.1, 153.9, 159.8.

From the results of X-ray crystal analysis, it has been found that oxanosine has the following structural formula:

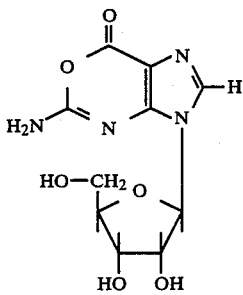

The biological activities of oxanosine are as follows.

1. Antimicrobial Spectrum:

The antimicrobial spectrum of oxanosine determined in 0.5% peptone agar is shown in Table 2. As is seen from Table 2, oxanosine has a relatively strong growth-inhibiting action against Gram-negative bacteria such as *Escherichia coli* K-12, *Escherichia coli* ML 1629 (multi-resistant strain), bacteria belonging to the genus Proteus and bacteria belonging to the genus Shigella, but it does not show growth-inhibiting action against Gram-positive bacteria.

TABLE 2

| Test Organism | Minimum Growth Inhibition Concentration (mcg/ml) |
|---|---|
| *Staphylococcus aureus* FDA 209P | >100 |
| *Staphylococcus aureus*, Smith strain | >100 |
| *Micrococcus flavis* FDA 16 | >100 |
| *Bacillus subtilis* PCI 219 | >100 |

TABLE 2-continued

| Test Organism | Minimum Growth Inhibition Concentration (mcg/ml) |
|---|---|
| *Bacillus subtilis* NRRLB-558 | >100 |
| *Sarcina lutea* PCI 1001 | >100 |
| *Corynebacterium bovis* 1810 | >100 |
| *Escherichia coli* NIHJ | >100 |
| *Escherichia coli* K-12 | 12.5 |
| *Escherichia coli* ML1629 (multi-resistant strain) | 25 |
| *Shigella dysenteriae* JS 11910 | 25 |
| *Shigella flexneri* 4B JS 11811 | 6.25 |
| *Shigella sonnei* JS 11746 | 25 |
| *Salmonella typhi* T-63 | >100 |
| *Salmonella enteritidis* 1891 | >100 |
| *Proteus vulgaris* OX 19 | 25 |
| *Proteus mirabilis* IFM OM-9 | 12.5 |
| *Proteus rettgeri* GN 311 | >100 |
| *Proteus rettgeri* GN 466 | 12.5 |
| *Serratia marcescens* | >100 |
| *Pseudomonas aeruginosa* A3 | >100 |
| *Klebsiella pneumoniae* PCI 602 | >100 |
| *Candida albicans* 3147 | >100 |
| *Mycobacterium smegmatis* 607 | >100 |

2. Anti-HeLa Activity

The results of examination of the anti-HeLa activity of oxanosine are shown in Table 3.

TABLE 3

| Concentration (mcg/ml) | Cells (× 10$^5$/plate)* | Percent Inhibition (%) | IC$_{50}$ (mcg/ml) |
|---|---|---|---|
| 100 | 1.08 | 100 | |
| 10 | 8.68 | 31.25 | Ca. 30.92 |
| 1 | 10.31 | 15.33 | |
| 0.1 | 11.70 | 1.76 | |
| 0 | 11.88 | — | |

Note:
*number of cells after 72 hours' culturing in the presence of oxanosine

As is apparent from Table 3, the anti-HeLa activity value (IC$_{50}$) of oxanosine of the present invention is about 30.92 mcg/ml.

3. Effect Against Mouse Leukemia L-1210:

Cells (1 × 10$^5$) of leukemia L-1210 were intraperitoneally implanted in each of several groups of 8-week-old female mice of the CDF series (5 mice for each group), a solution of oxanosine in a physiological saline solution was intraperitoneally administered once each day for 9 days, and the carcinostatic effect was evaluated based on the life-prolonging effect (T/C, %). The results of this test are shown in Table 4. It is seen that oxanosine has a life-prolonging effect in leukemia L-1210 tumor-bearing mice.

TABLE 4

| Dose (μg/mouse/day) | Life-Prolonging Effect (T/C, %) |
|---|---|
| 1000 | 160 |
| 500 | 153 |
| 250 | 120 |
| 125 | 120 |
| 62.5 | 100 |
| 0 | 100 |

4. Acute Toxicity in the Mouse:

The acute toxicity (LD$_{50}$) of oxanosine in the mouse is larger than 200 mg/kg (iv), and it is seen that the acute toxicity of oxanosine is lower than those of various known nucleic acid type antibiotic substances.

As with other antibiotics, the dosage regimen for oxanosine will depend on the weight, age, sex and general health of the patient, as well as the nature and severity of the disease. In general, the dosage of oxanosine for an adult human will be in the range of 50–1000 mg, given 1–4 times per day.

The present invention will be described in detail with reference to the following example that by no means limits the scope of the invention. Various modifications and changes may be made, subject only to the limitations of the claims.

EXAMPLE 1

Sakaguchi flasks (500 ml capacity) for a reciprocating type shaking machine were charged with 125 ml of a culture medium (pH value=7.0) comprising 1% of glucose, 1% of glycerol, 1% of sucrose, 0.5% of oat meal, 2% of soybean meal (Prorich supplied by Ajinomoto K.K.), 1% of pressed yeast (supplied by Oriental Kobo Kogyo K.K.), 0.5% of Casamino acid (supplied by Difco Co.) and 0.1% of calcium carbonate, and the culture medium was sterilized at 120° C. for 20 minutes in an autoclave. The culture medium in each was inoculated with one platinum loop of MG265-CF3 (Fermentation Research Institute Deposit No. 5735), and culturing was carried out for 2 days at 28° C. with shaking at 120 rpm. Separately, 500 ml capacity Erlenmeyer flasks (with a baffle) for a rotary type shaking machine were each charged with 120 ml of a culture medium (pH value=7.4) comprising 2% of galactose, 2% of dextrin, 1% of Bacto-Soytone (supplied by Difco Co.), 0.5% of corn steep liquor (supplied by Ajinomoto K.K.), 0.2% of ammonium sulfate, 0.2% of calcium carbonate and 0.05% of a 1:1 mixture of Silicone KM-70 (supplied by Shinetsu Kagaku Kogyo K.K.) and soybean oil (Japanese Pharmacopoeia), and the culture medium was sterilized at 120° C. for 20 minutes in an autoclave. Then, 12 ml of the first-mentioned culture medium was added to the charge of each of the flasks and culturing was conducted at 28° C. for 5 days with shaking at 180 rpm. The culture broths were filtered at a pH value of 6.5 to obtain 11 liters of filtrate. (The titer was determined according to the cup method using *Escherichia coli* K-12 as a test organism on peptone-agar plate, and the titer of the culture filtrate was designated as $1\mu$/ml.) The filtrate was passed through a column packed with 500 ml of active carbon powder for chromatography (supplied by Wako Junyaku) to absorb the oxanosine on the active carbon. The column was washed with water and elution was carried out according to the acetone linear concentration gradient elution method using 1500 ml of water and 1500 ml of 50% aqueous acetone. Active fractions were collected, concentrated under reduced pressure and freeze-dried to obtain 3.56 g of dark brown crude powder ($3\mu$/mg). The powder was then treated with 85 ml of methanol, and the soluble portion was dried under reduced pressure to obtain 1.29 g of brown crude powder ($7\mu$/mg). This powder was dissolved in 43 ml of water and the oxanosine was adsorbed on a column packed with 180 ml of active carbon powder. The column was washed with water and elution was carried out according to the acetone linear concentration gradient elution method using 400 ml of water and 400 ml of 50% aqueous acetone. Active fractions were collected, concentrated under reduced pressure and freeze-dried to obtain 294 mg of pale brown powder ($28\mu$/mg). This powder was dissolved in 11 ml of water, and the solution was charged on a column packed with 600 ml of Avicel ® equilibriated with ethanol/water (95/5). Then elution was carried out with 1200 ml of ethanol/water (95/5) and then with 1200 ml of ethanol/water (90/10). Active fractions were collected, concentrated under reduced pressure and freeze-dried to obtain 82.8 mg of pale brownish powder ($95\mu$/mg). The powder was dissolved in 6.4 ml of warm water and the solution was allowed to cool overnight. There was obtained 64.9 mg of oxanosine in the form of slightly grayish needle crystals ($117\mu$/mg).

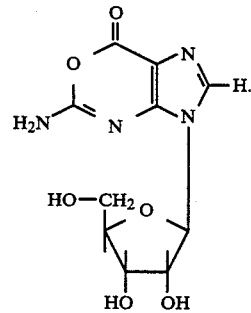

We claim:
1. The antibiotic oxanosine having the formula